US005824310A

United States Patent [19]
Golding

[11] Patent Number: 5,824,310
[45] Date of Patent: Oct. 20, 1998

[54] LIPOPPLYSACCHARIDE CONJUGATE VACCINES

[75] Inventor: Basil Golding, Rockville, Md.

[73] Assignee: The United States of America as represented by the Department of Health and Human Services, Washington, D.C.

[21] Appl. No.: 369,565

[22] Filed: Jan. 6, 1995

Related U.S. Application Data

[63] Continuation of Ser. No. 780,205, Oct. 22, 1991, abandoned.
[51] Int. Cl.$^6$ .................. A61K 39/385; A61K 39/21; C07K 17/00
[52] U.S. Cl. ........................ 424/193.1; 424/194.1; 424/196.11; 424/197.11; 424/208.1; 530/403; 530/807
[58] Field of Search .................. 530/403–406, 530/807; 424/193.1, 194.1, 196.11, 197.11, 208.1

[56] References Cited

U.S. PATENT DOCUMENTS

| | | | |
|---|---|---|---|
| 4,693,891 | 9/1987 | Collins et al. | 424/92 |
| 4,789,544 | 12/1988 | Nelson et al. | 424/92 |
| 4,831,126 | 5/1989 | Bundle et al. | 536/53 |
| 4,834,975 | 5/1989 | Siadak et al. | 424/87 |
| 4,929,604 | 5/1990 | Munford et al. | 514/53 |
| 5,006,463 | 4/1991 | Cherwonogrodzky | 435/7.32 |

FOREIGN PATENT DOCUMENTS

| | | | |
|---|---|---|---|
| 9101750 | 2/1991 | WIPO | A61K 39/02 |

OTHER PUBLICATIONS

Journal of Biological Response Modifiers 3:1–9 copyright 1984 Raven Press, New York, pp. 1–9.
Biological Activities of Monophosphoryl Lipid A, Edgard Ribi, John Cantrell, Tim Feldner, Kent Myres and Jon Peterson, Ribi ImmunoChem Research, Inc., Hamilton, Montana 59840, pp. 9–13.
Federation of American Societies for Experimental Biology, 75th Annual Meeting, Atlanta, Georgia, Apr. 21–25, 1991, Part II, pp. 1 and 2. Abstract No. 3670 Goldstein et al.
Phillips et al American Journal of Veterinary Research, vol. 50, No. 3, Mar. 1989, pp. 311–318.
Analytical Biochemistry 119, 115–119 (1982) A sensitive Silver Stain for Detecting Lipopolysaccharides in Polyacrylamide Gels, Chao–Ming Tsai and Carl E. Frasch.
The Journal of Biological Chemistry, vol. 350, No. 8, Issue of Apr. 25, pp. 2911–2919, 1975, Fractions of Lipopolysaccharide from Escherichia coli 0111:B4 Prepared by Two Extraction Procedures, Morrison and Leive.
Journal of Biological Response Modifiers 6:99–107, copyright 1987 Raven Press, New York, "The Adjuvant Properties of a Nontoxic Monophosphoryl Lipid A in Hyporesponsive and Aging Mice", Tomai, Solem, Johnson and Ribi.
Ribi Biological Response Modifiers, Ribi Immunochem Research, Inc.
Immunopharmacology of Infectioous Diseases: Vaccine Adjuvants and Modulators of Non–Specific Resistance, pp. 101–112, copyright 1987 Alan R. Liss, Inc. Ribi et al.
Modulation of Humoral and Cell Mediated Immune Responses By a Structurally Established Nontoxic Lipid A, pp. 407–420, Ribi et al, in Immunobiology and Immunopharamacology of bacterial Endotoxins, Szentivanyi et al Eds, Plenum Press New York, 1996.
Technological Advances in Vaccine Development, pp. 443–454, copyright 1988 Alan R. Liss, Molecularly Engineered Microbial Immunostimulators, Jon A. Rudbach, John L. Cantrell and J. Terry Ulrich, pp. 443–454.

(List continued on next page.)

Primary Examiner—Ponnathapura Achutamurthy
Attorney, Agent, or Firm—Needle & Rosenberg, PC

[57] ABSTRACT

The present invention relates to lipopolysaccharides from *Brucella abortus* and their use as carriers in vaccines for humans and animals. In particular, the present invention relates to conjugate molecules having a carrier molecule of purified lipopolysaccharide from *B. abortus* coupled to an antigenic component of an infectious organism.

4 Claims, 9 Drawing Sheets

OTHER PUBLICATIONS

The Journal of Immunology, Copyright 1984 by The American Association of Immunologists, vol. 133, No. 6, Dec. 1984, Newborn And Wiskott–Aldrich Patient B Cells Can Be Activated By TNP–Brucella Abortus:Evidence . . . Antigen In Humans, B. Golding, A. V. Muchmore and R. M. Blaese.

The Journal of Immunology, Copyright 1981 by The Williams & Wilkins Co., vol. 127, No. 1, Jul. 1981, "Human Lymphocytes Can Generate Thymus–Independent As Well . . . In Vitro[1] " B. Golding et al.

Gregory Gregoriadis eds *Immunological Adjuvants and Vaccines* by Rietschel et al "Bacterial endotoxins: Relationship between Chemical Structure and Biological Activity" Ser. A vol. 179:61–74.

Lambden et al (1982) J. Immunol. Methods 48:233–240.

Louis et al (1979) Springer Semin. Immunopatho 12:215–228.

Ribi et al (1984) Reviews of Infectious Dis. 6(4):567–572.

Galanos et al (1977) International Review of Biochemistry, Biochemistry of Lipids II, vol. 14:239–333.

Berger et al. (1969) Proc. Soc. Exp. Biol. Med. 131:1376–1381.

Alonso–Urmeneta et al (1988) J. Clin. Microbiol. 26(12):2642–2646.

Golding et al (1991) AIDS Research Human Retroviruses 7(5):435–446.

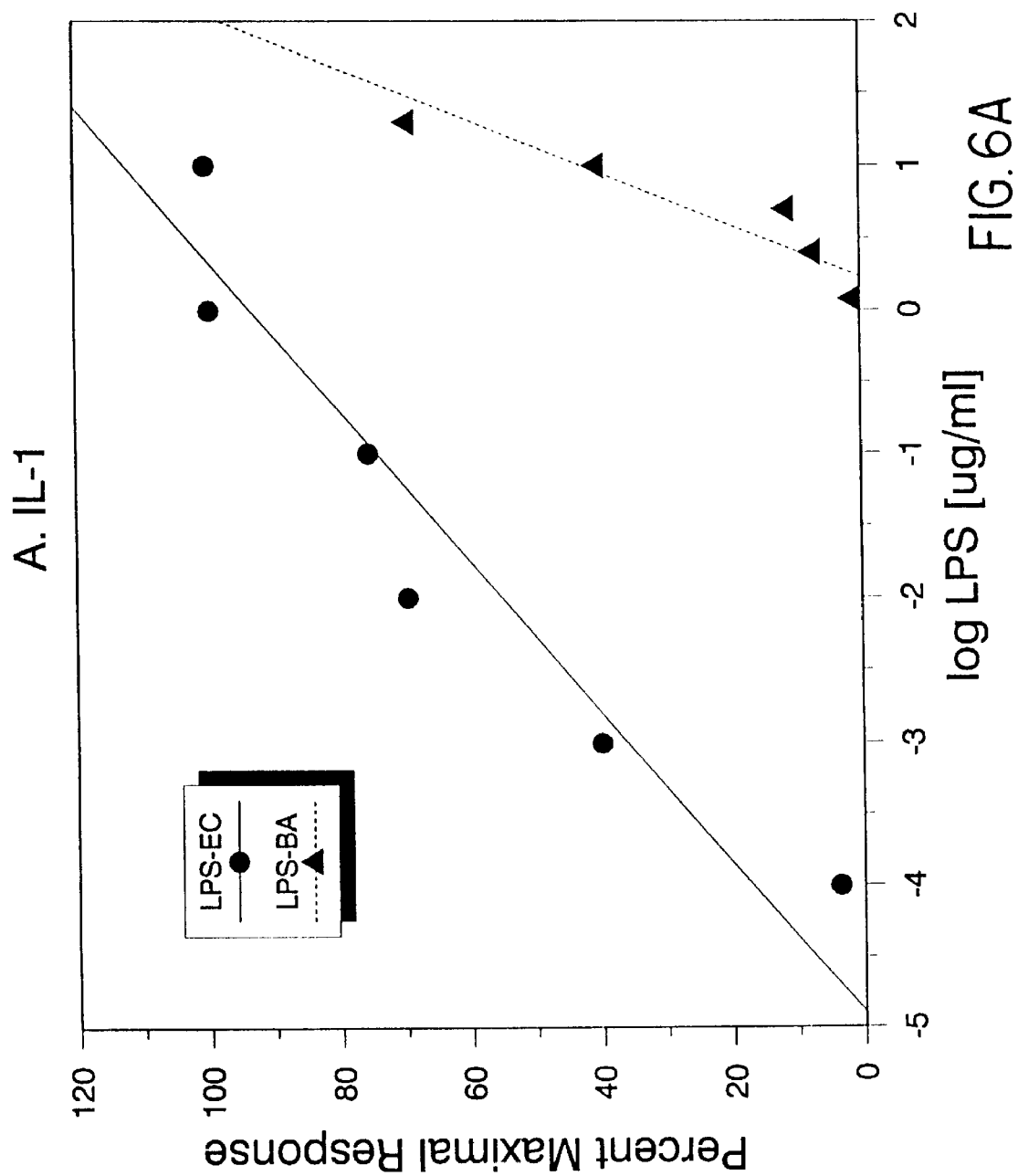

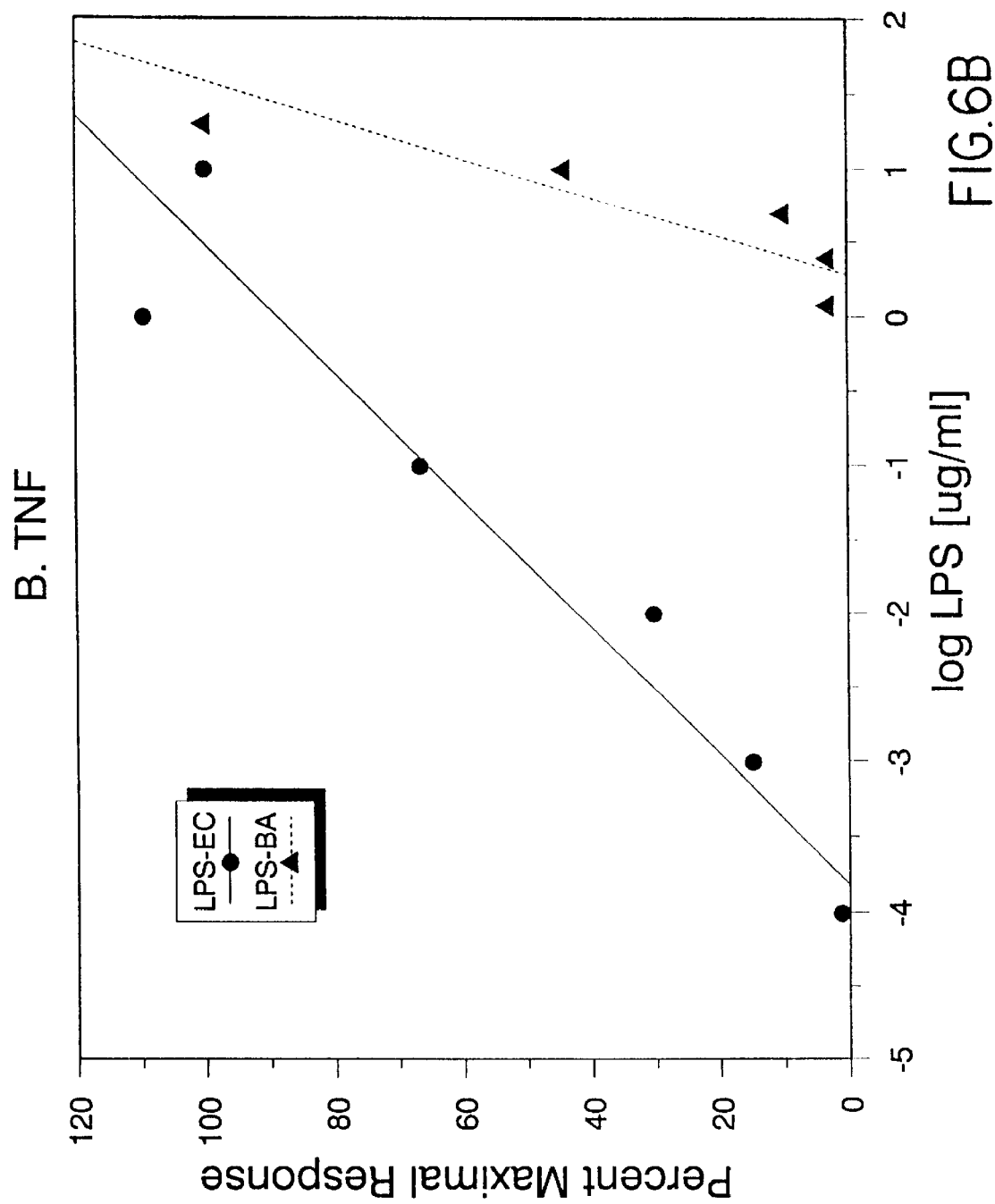

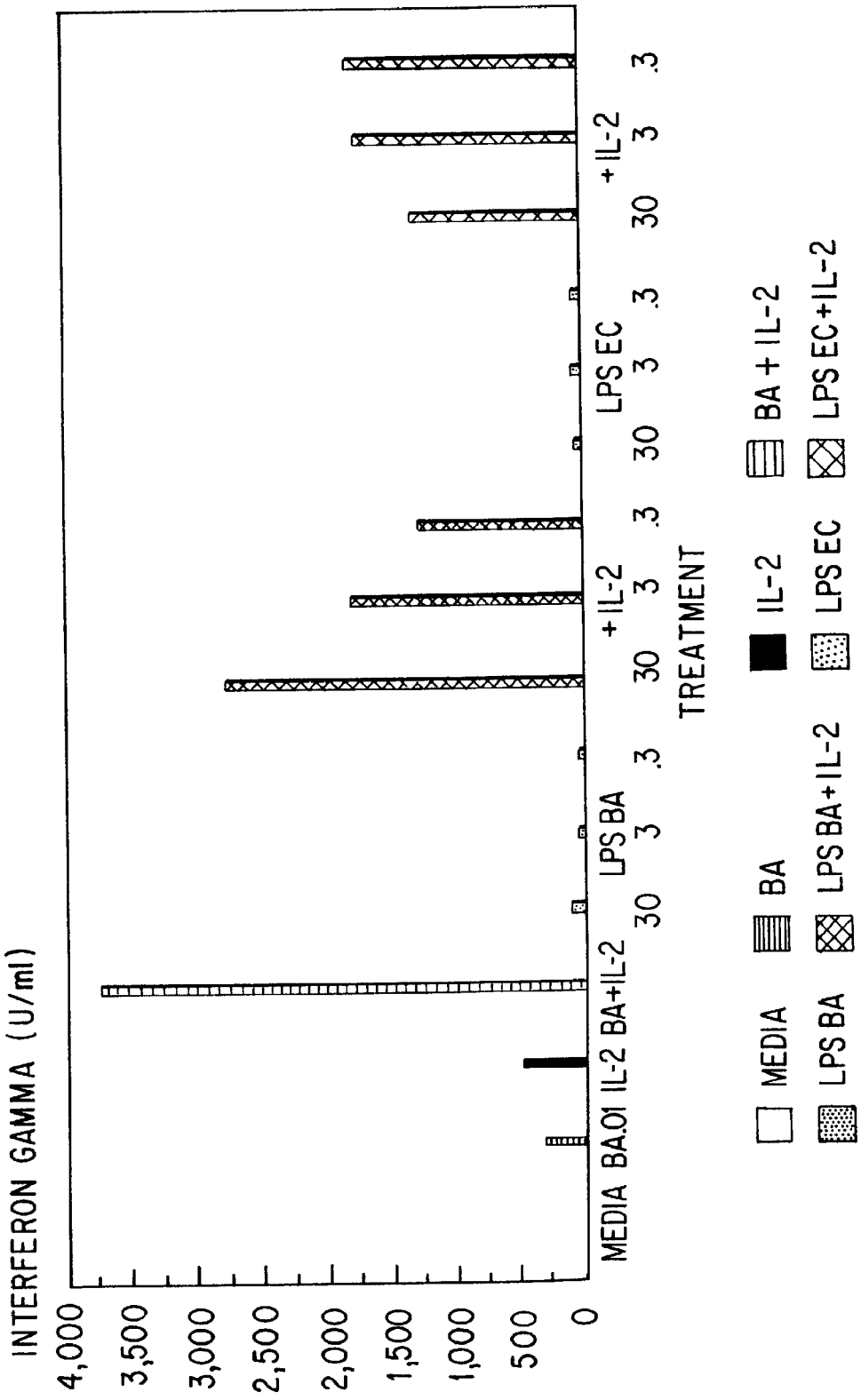

5,824,310

LIPOPPLYSACCHARIDE CONJUGATE VACCINES

This application is a continuation of application Ser. No. 07/780,205, filed Oct. 22, 1991, abandoned.

BACKGROUND OF THE INVENTION

1. Field of the Invention

The present invention relates to lipopolysaccharides (LPS) from *Brucella abortus* and the use of such LPS as carriers in vaccines.

2. Background Information

Bacterial endotoxins or lipopolysaccharides, constitutive components of gram negative bacteria cell walls, are macromolecules composed of three regions: O-chain, core and lipid A. Chemically *Brucella abortus* (BA) LPS has unique characteristics that may be responsible for its immunogenic qualities. The O-chain is comprised of linear $\alpha$-1,2 linked unbranched homopolymers of single glycose repeating units, with a length that ranges from 96 to 100 units. The core, composed of the trisaccharide keto-deoxy-octonate (KDO) links the lipid to the polysaccharide. The lipid A of this bacteria is characterized by a large proportion of long chain saturated fatty acids (>C16), very small amounts of hydroxylated fatty acids, no $\beta$-OH myristic acid and a different proportion of amide and ester linked fatty acids from that found in enterobacteria such as *E. coli* (LPS-EC), (Marx et al., 1983 Zbl. Bakt. Hyg., I. Abt. Orig. 253:544–553; Moreno et al., 1979 J. Bact. 138:361–369; and Meikle et al., 1989 Inf. Immun 57:2820–2828).

At the cellular level, *Brucella abortus* has been shown to behave as a T-independent type 1 carrier (TI-1) in the activation of human B cells. When conjugated to trinitrophenyl (TNP) it is capable of stimulating antibody responses in adult as well as in neonatal human B cells (Golding et al., 1981 J. Immunol. 127:220–224; Golding et al., 1990 Vaccines 90:249–253). Previous experiments demonstrated that HIV-1 conjugated to BA was able to induce murine antibody responses in the relative absence of CD4+T cells (Golding et al. 1991 AIDS Research and Human Retroviruses 7:435–446), suggesting that BA may be used as a carrier for vaccines in HIV-individuals in whom CD4+T cells are depleted.

Current human vaccines against infectious organisms consist of an attenuated or inactive form of the organism mixed with adjuvant. Vaccines have also been prepared using polysaccharide antigens complexed to proteins. The advantage of the latter approach is that proteins enhance human infant antibody responses to polysaccharides. Similar to protein carriers, when used as a carrier, BA can evoke antibody responses in human newborn B cells. In contrast to protein carriers, BA is less dependent on T cells for help in antibody production. Thus, BA can be used in certain immunodeficiency states, such as following HIV-1 infection, which are associated with T helper cell impairment.

A potential problem, however, with the use of BA as a carrier is that lipopolysaccharides induce endotoxic shock which is associated with IL-1$\beta$ and TNF-$\alpha$ release. These monokines are synthesized and liberated from monocytes/macrophages in response to LPS, microbial invasion, tissue injury, immunologic reactions and inflammatory processes (Dinarello C. A., 1988 FASEB J. 2:108–115; Carswell et al., 1975 Proc. Natl. Acad. Sci. U.S.A. 72:3666-70; Beutler et al., 1985 Nature. 316:552–554) and are implicated in the pathogenesis of the acute-phase response during endotoxic shock (Dinarello C. A., 1987 N. Engl. J. Med. 311:1413–1418; Beutler et al, 1987 N. Engl. J. Med. 316:379–385; Permutter et al., 1986 J. Clin Invest. 78:1349–1354). For BA to be used successfully in vaccines for humans, a form which does not induce endotoxic shock is required.

SUMMARY OF THE INVENTION

Accordingly, it is an object of the present invention to provide a carrier which does not induce endotoxic shock.

Various other advantages and objects of the present invention will become apparent from the following drawing and description of the invention.

In one embodiment, the present invention relates to a conjugate molecule comprising a carrier molecule of purified lipopolysaccharide (LPS) from *Brucella abortus*, coupled to an antigenic component.

In another embodiment, the present invention relates to a vaccine for humans comprising the conjugate molecule of the present invention and a pharmaceutically acceptable vehicle and/or adjuvant.

In a further embodiment, the present invention relates to a method of vaccinating a patient against an infectious organism comprising administering to the patient an immunogenic amount of the conjugate of the present invention specific for the infectious organism in a pharmaceutically acceptable vehicle and/or adjuvant.

BRIEF DESCRIPTION OF THE FIGURES

FIG. 6A is a comparison of effect of LPS-BA and LPS-EC on human monocyte secretion of IL-1$\beta$.

FIG. 6B is a comparison of effect of LPS-BA and LPS-EC on human monocyte secretion of TNF-$\alpha$.

FIG. 8 shows the interferon gamma produced by T cells stimulated with LPS+IL-2.

DETAILED DESCRIPTION OF THE INVENTION

Figure 1:
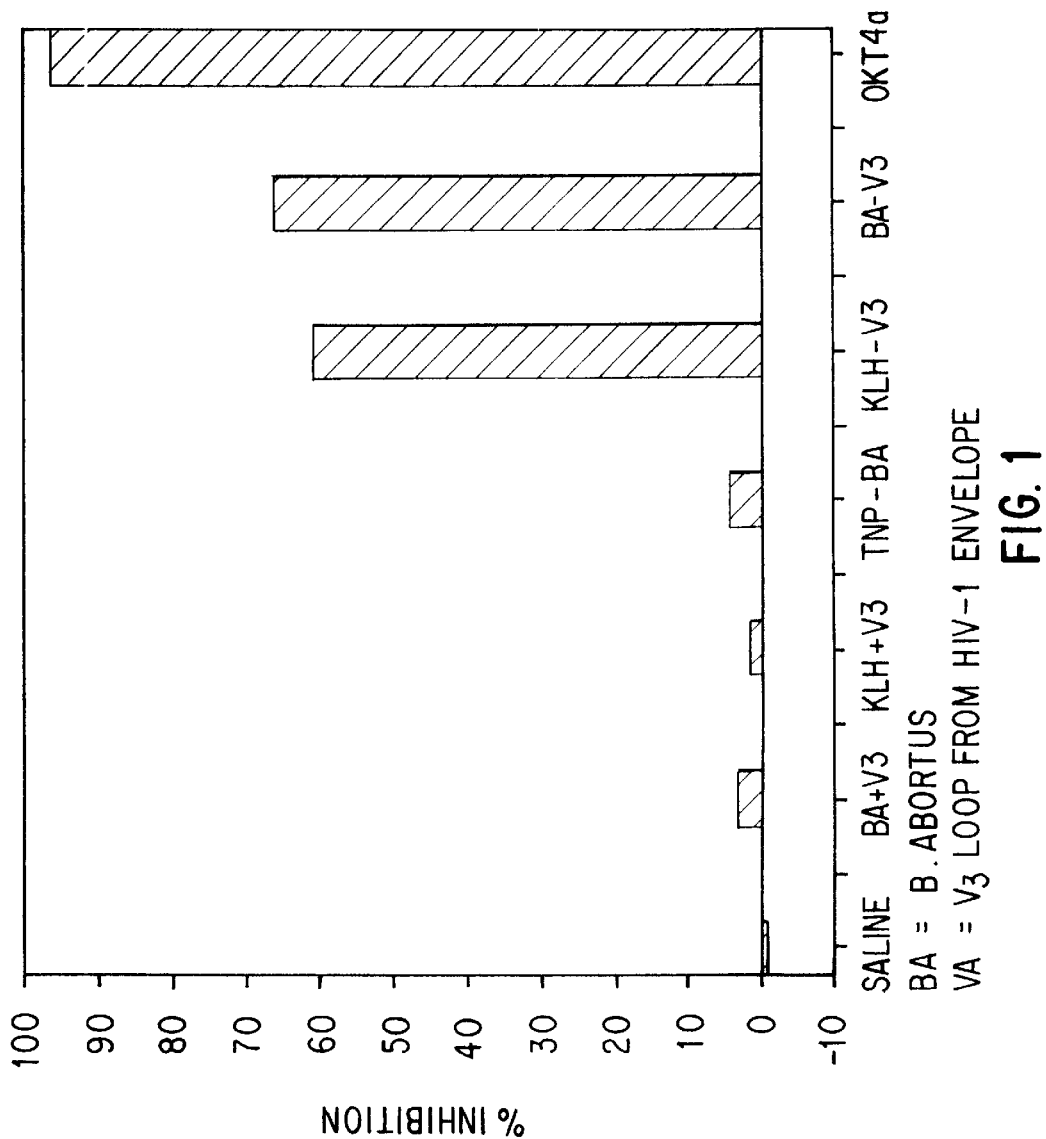
FIG. 1 shows syncytia inhibition by sera from mice immunized with $V_3$ conjugates. V3 in this context is a hexapeptide derived from the third variable region of gp120 (envelope protein of HIV-1). Mice were immunized with the V3 conjugates every two weeks for three injections and bled five days after the last injection. Sera from these mice were tested for ability to inhibit syncytia. The syncytia are formed by gp120 from HIV-1 interacting with CD4 on target T cells.

Whether LPS derived from BA is safe for human use is of interest because BA has unique properties in stimulating human T and B cells (Golding et al., 1984 J. Immunol. 1336:2966–2971; Golding et al., 1981 J. Immunol. 127:220–224). Unlike other gram negative bacteria, BA is capable of stimulating human B cells, including human newborn B cells (Golding et al., 1981 J. Immunol. 127:220–224; Golding et al., 1990 Vaccines 90:249–253), which makes it suitable for use as a carrier. This B cell stimulation occurs in a T cell independent manner.

Further, BA-HIV-1 conjugates are able to induced murine antibody responses in the relative absence of $CD_4^+$T cells (Golding et al. 1991 AIDS Research and Human Retroviruses 7:435–446). BA conjugated to HIV-1 was also shown to be immunogenic in mice (Golding et al. 1991 AIDS Research and Human Retroviruses 7:435–446). Sera from mice immunized with BA conjugated with the $V_3$ loop of the HIV-1 envelope can also inhibit syncytia formation as shown by the present inventor (see FIG. 1).

In addition to stimulating B cells, BA can stimulate human T cells (both CD4+ and CD8+ T cells) causing the secretion of gamma interferon (IFNg) (see FIGS. 2 and 3). As IFNg has pleiotropic effects, many of which would favor protection against viral infection, the stimulation of its production make BA a potential carrier for human vaccines. These pleiotropic effects include macrophage activation (Schultz et al., 1983 Nature 305:239–243 and Stabbing et al., 1987 p. 87, In Mechanism of Interferon Actions Vol. II, L. M. Pfeffer (ed) CRC Press); upregulation of MHC class II antigen expression (Wallach et al., 1982 Nature 299:833–836 and Sztein et al., 1984 J. Clin. Invest. 73:556–565); increased differentiation of murine B cells (Sidman et al., 1984 Nature 309:801–804) and monocyte-depleted human B cells (Golding et al., 1986 J. Immunol 137:103–107), switching of Ig in the mouse to IgG2a (Snapper et al., 1987 Science 236: 944–947; Snapper et al., 1988 J. Immunol. 140: 2121–2127; Finkelman et al., 1988 J. Immunol. 140: 1022–1027), direct anti-viral effects (Weigent et al., 1983 Infect. and Imm. 40:35–38); and potentiation of lymphocyte natural killing (Weigent et al., 1983 Infect. and Imm. 40:35–38 ).

IFNg is a product of CD4+ and CD8+ T cells. CD4+ T cells have been classified in mice as TH0, TH1 or TH2, depending on the pattern of cytokines they secrete (Mosmann et al., 1989 In Advances in Immunology vol. 46, Dixon (ed) Academic Press, San Diego p. 111–147). TH1 cells secrete IL-2 and IFNg, whereas TH2 cells secrete IL-4 and IL-5. TH0 cells secrete both sets of cytokines. Recent studies with human T cell clones have shown that the same TH subsets occur in humans (Romagnani et al., 1991 FASEB J. 5: A1337). Since BA induces IFNg and IL-2 secretion, it probably activates human TH1 cells. This is in accordance with in vivo murine studies which showed that repeated immunization with BA led to preferential expansion of TH1 clones (Street et al., 1990 J. Immunol. 144:1629–1639).

The ability of BA to favor switching to IgG2a in the mouse is probably the result of TH1 stimulation and is probably mediated by IFNg (Snapper et al., 1987 Science 236: 944–947; Snapper et al., 1988 J. Immunol. 140: 2121–2127; Finkelman et al., 1988 J. Immunol. 140: 1022–1027; Golding et al., 1991 AIDS and Human Retrovirus 7: 471–482; Street et al., 1990 J. Immunol. 144: 1629–1639). IgG2a may be the preferred isotype in the mouse for protection against intracellular infections by bacteria such as BA or viruses because IgG2a has a greater ability than other murine isotypes to bind Fc receptors and mediate ADCC reactions (Unkeless et al., 1977 J. Exp. Med. 145:931–947) and to activate complement (Johnson et al., 1984 In Mechanisms of cell-mediated cytoxicity II. p. Henkart and E. Martz (ed) Plenum, N.Y. p. 75–84).

A primary concern with the use of BA is related to the potential of LPS to induce endotoxic shock. Endotoxic shock is probably due to the stimulation of monocytes which release IL-1 and tumor necrosis factor (TNF) (Dinarello C. A. 1988 FASEB J. 2:108–115; Carswell et al., 1975 Proc. Natl. Acad. Sci. U.S.A. 72:3666-70; Beutler et al., 1985 Nature, 316:552–554; Dinarello C. A., 1987 N. Engl. J. Med. 311:1413–1418; Beutler et al., 1987 N. Engl. J. Med. 316:379–385; Permutter et al., 1986 J. Clin. Invest. 78:1349–1354). TNF alters the hemostatic properties of the vascular endothelium, inducing the production of procoagulant activity and inhibiting the expression of thrombomodulin at the cell surface (Nawroth et al., 1986 J. Exp. Med. 163:740–745; Bevilaqua et al., 1986 Proc. Natl. Sci. USA. 83:4533–4537). This favors the accretion of thrombi leading to disseminated intravascular coagulation (Beutler et al., 1987 N. Engl. J. Med. 316:379–385). TNF also increases IL-1 production. IL-1 stimulates the synthesis of the hepatic acute phase proteins in particular protease inhibitors, complement components and fibrinogen (Dinarello C. A., 1988, FASEB J., 2:108–115; Dinarello C. A., 1987 N. Engl. J. Med. 316:379–385). It induces fever and leukocytosis; enhances phagocytosis, chemotaxis, lysosomal degranulation, stimulated $PGE_2$ release in monocytes and neutrophils and increases proliferation of fibroblasts and T lymphocytes.

The present inventor has discovered that LPS from BA retains many of the BA properties and thus appears to be the active component of BA. For example, LPS-BA retains the ability to stimulate T cells to make cytokines in vitro. It is also likely that LPS-BA will stimulate human B cells in a manner similar to the complete bacteria. LPS-BA is also active as an immunogen in mice and is an effective carrier. Further, LPS from BA is less pyrogenic and less likely to induce endotoxic shock than LPS from other species which makes it particularly suitable for use as a carrier in human vaccines. Due to the properties of the BA LPS and its role as an active component of BA, it is likely that it can be used in human vaccines.

Accordingly, the present invention relates to a carrier which can elicit responses against an antigen. For example, an antigen of an infectious organisms or a self-tumor antigen. As used herein, a carrier is defined as a foreign molecule which serves as an immunogenic agent to which an antigen (epitope) is coupled to form a conjugate. When conjugates are administered to a patient an immune response against the antigen is induced. Conjugates of the present invention can be used in vaccines to induce protective immunity against various organisms, to induce antibodies against self or syngeneic tumors (Talmadge et al., 1984 Behringer Inst. Mitt. 74:189) or to induce antibodies against biologic effector molecules.

In one embodiment, the present invention relates to a carrier comprising purified lipopolysaccharide (LPS) of *Brucella abortus*. LPS can be purified using standard methods known in the art, for example, see Morrison and Leive, 1978 J. Biol. Chem. 250:2911–2919. Preferably, the LPS carrier is purified at least 95%, more preferably at least 98%. The LPS-BA carrier may be used as an adjuvant. Further, LPS-BA is a suitable carrier for use in human vaccines as it is less pyrogenic in rabbits (about 10,000 fold less) than LPS derived from *E. coli* and less likely to induce lethality (about 268 fold less) than LPS-EC as shown in mice. Moreover, LPS derived from *E. coli* is 1400 fold more potent in inducing IL-1β production and 400 fold more potent in inducing TNF-α production from human monocytes. As IL-1β and TNF-α production correlates with induction of endotoxic shock, LPS-BA is less likely than LPS-EC to induce endotoxic shock in humans.

In another embodiment, the present invention relates to immunogenic conjugates prepared using the carrier of the present invention. Conjugates of the present invention are prepared by using standard coupling techniques to link the LPS-BA carrier to an antigenic component. For example, the carrier and the component can be coupled via heteroligation using thio-ester linkages. Alternatively, protein or sugar components derived from the infectious organism can be linked to the carrier via a free amino group on the LPS-BA. In the case of proteins, thiol conjugates can be made using a cysteine group on the protein or peptide molecule.

Examples of suitable antigenic components include, but are not limited to, components of an infectious organism (for example, a virus or bacterium), a tumor specific antigen or a biological effector molecule. Components from an infectious organism are selected so that antibodies against them can neutralize the organism. Suitable components include, but are not limited to, proteins, multiple peptides or single peptides. Conjugates of the present invention are more immunogenic than the infectious organism or a component thereof because of the unique properties of the LPS-BA carrier.

In a further embodiment, the present invention relates to vaccines for use in humans and animals. Conjugates of the present invention are especially suitable for use in human vaccine as they are not likely to be associated with the induction of endotoxic shock. Accordingly, vaccines of the present invention include at least one conjugate of the present invention in a pharmaceutically acceptable vehicle and/or adjuvant known in the art. Examples of suitable carriers include, but are not limited to, lipopolysaccharide from *B. abortus*, lipid A from this latter LPS, modified lipid A and inactivated *B. abortus*. The vaccine may also include an adjuvant, such as, for example, alum, MPL (Ribi) and Syntex adjuvant, which act to increase the immunogenicity of the conjugate. The vaccine may also include other auxiliary agents such as cytokines (e.g. interferon gamma) to promote isotype switching.

The vaccines of the present invention can be used, for example, against infectious organisms, self or syngeneic tumors, or biological effector molecules to control physiological processes. conjugates for use in vaccines against self or syngeneic tumors (such as, melanomas) can be generated by coupling a tumor specific antigen to LPS-BA. Further, vaccines for controlling physiological processes can be generated by inducing an autoimmune response against biological effector molecules using conjugates of the present invention. For example, animal vaccines can be generated to increase fertility or growth using conjugates of the present invention. Such vaccines would induce the formation of antibodies against, for example, inhibin (for fertility) or somatostatin (for growth).

The vaccination treatments may consist of a single administration or a series of administrations. The vaccine of the present invention can be administered via subcutaneous or intramuscular routes. The conjugate is present in the vaccine in an amount sufficient to induce an immune response against the organism component of the conjugate and thus protect against infection with that organism. Dosages given a patient will vary depending on several factors, such as condition of patient and route of administration. (Generally, however, a patient is vaccinated with about 50 $\mu g/m^2$ of conjugate.) These doses can be more accurately determined in non-human primate and human studies by those skilled in the art.

The vaccines of the present invention can consist of conjugates against one or more infectious organisms. For example, such organisms include, but are not limited to HIV-1, cytomegalovirus, herpes viruses and bacterial capsular polysaccharides.

LPS from BA was purified and compared with LPS from *E. coli* in its ability to induce fever in rabbits, endotoxic shock and lethality in mice, and release of IL-1β and TNF-α from human monocytes. LPS-BA was considerably less potent that LPS-EC in all three instances. Thus LPS-BA was (i) $10^4$ fold less potent than LPS-EC in elevating the temperature of rabbits, (ii) 268-fold less potent in causing endotoxic shock and death in mice and (iii) 1400-fold and 400-fold less potent, in eliciting IL-1β and TNFα production in human monocytes, respectively.

EXAMPLE

The following non-limiting examples are provided to further describe the present invention.

IFNg Production by BA-stimulated Peripheral Blood T Cells

To determine whether human T cells could secrete IFNg in response to BA, human mononuclear cells (MNC) were enriched for T cells by resetting with sheep red blood cells (SRBC) as described below and incubated with heat-inactivated BA ($10^8$ organisms/ml).

T cells were prepared by subjecting buffy coats from the peripheral blood of normal and HIV-1 infected individuals to centrifugation through Ficoll-Paque (Pharmacia, Piscataway, N.J. to obtain mononuclear cells (MNC). The cells were cultured in RPMI medium supplemented with 10% human AB serum, 2 mM L-glutamine and 1% penicillin-streptomycin (all from GIBCO, Grand Island, N.Y.). Cells were cultured in 96 well plates (Costar, Cambridge, Mass.) at $10^6$ cells per well in 0.2 ml of medium, unless otherwise noted. Recombinant human IL-2 (Genzyme, Boston, Mass.) was added to cultures in some experiments.

Macrophages were depleted from mononuclear cell preparations by filtration through SEPHADEX G-10 (Pharmacia, Piscataway, N.J.) as described by Ly and Mishell (Ly et al., 1974 J. Imm. Methods 5:239–247). The number of monocytes/macrophages before and after Sephadex filtration was determined by flow cytometry using fluorescein isothiocyanate (FITC)-conjugated mouse monoclonal antibodies against human CD3 (Leu-4), CD4 (Leu-2a), CD8 (Leu-3a), CD14 (Leu-M3), CD16 (Leu-11a), CD19 (Leu-12), and CD25 (IL-2R, p55) antigens, respectively (Becton Dickinson Immunocytometry Systems, Mountain View, Calif.).

Briefly, the cells were adjusted to a concentration of $2 \times 10^7$ cells/ml in buffer (PBS plus 1% BSA plus 0.02% NaN3). Fifty ul of these cells ($10^6$ cells) were then mixed with 20 ul of the relevant FITC-conjugated antibody in 12×75 mm test tubes and incubated on ice in the dark for 30 minutes. The cells were then washed twice, resuspended in 0.5 ml of buffer and filtered through nylon gauze. The cells from HIV-1 infected persons were fixed with 0.1% paraformaldehyde to reduce the risk of contamination. Cells were analyzed by flow microfluorimetry using the FACScan system (Becton Dickinson Immunocytometry Systems, Mountain View, Calif.). The flow cytometer is a 15 milliwatt air-cooled argon-ion laser exciting at 488 nm and utilizing a 530 nm band pass filter.

T cells were enriched from MNC by rosetting with SRBC (NIH Media Unit) treated with a 1:20 dilution of neuraminidase Type II derived from Vibrio choleras, (Sigma, St. Louis, Mo.). Rosetted T cells were 85–95% pure as determined by flow microfluorimetry using anti-CD3 antibody.

T cells were separated into CD4+ (T helper cells) or CD8+ cells (T cytotoxic/suppressor cells) by panning, as described by Engleman et al. (Engleman et al., 1981 J. Immunol. 127:2124–2129). Bacteriological grade petri plates (Falcon 1029, Becton Dickinson Labware, Lincoln Park, N.J.) were coated for 60 minutes at room temperature with 10 ml of goat anti-mouse IgG antibody at 10 ug/ml (Organon-Teknika, Cappell #02110081, West Chester, Pa.) in 0.05M Tris or PBS, pH 7.2–7.5. Unbound antibody was removed with three washes of PBS and one wash with PBS containing 1% fetal calf serum (FCS).

Each T cell pellet containing $2–3 \times 10^7$ cells was mixed with 20 ul of anti-Leu-3a (anti-CD4) or anti-Leu-2a (anti-CD8) antibody (Becton Dickinson, Mountain View, Calif.) and incubated at room temperature for 20 minutes. The cells were then centrifuged, washed three times, resuspended to $2–3 \times 10^7$ cells in 3 ml of PBS plus 5% FCS, poured onto one antibody-coated plate and incubated for 1–2 hours at room temperature.

The negatively selected cells (the unbound fraction) were collected by decanting the plate and gently washing the plate with PBS plus 1% FCS. These negatively selected cells were then washed in media and resuspended to working concentrations. The actual percentages of CD4+ or CD8+ T cells in these purified populations were determined by flow microfluorimetry. In some experiments anti-Tac was added at 10 ug/ml.

The enriched T cells (E+) contained 85–95% CD3+ T cells, 2–5% B cells, 2–5% monocytes and 3–5% NK cells; whereas the unrosetted MNC contained 50–70% CD3+ cells, 5–10% B cells, 12–18% monocytes and 5–10% NK cells.

The presence of human IFNg in cell culture supernatant was measured by ELISA (AMGEN, Thousand Oaks, Calif.). Briefly, samples and standards were added to wells of an ELISA plate coated with a mouse monoclonal antibody to human IFNg. After incubation for 1 hr. at 37° C., the plates were washed four times with PBS (containing 1% Tween). A detector complex consisting of a biotinylated second monoclonal antibody to human IFNg and an anti-biotin/alkaline phosphatase conjugate was added to the wells for 1 hr at 37° C. The plates were then washed and phosphatase substrate added to the wells for 30 min. at 37° C., and the reaction stopped with NaOH. The optical density was read at 405 nm, and the concentration of IFNg in each sample determined by interpolation from the standard curve obtained using the standards provided with the kit, IFNg concentration was expressed in units/ml where the units were defined according to NIH HuIFN gamma standard Gg-23-901-530.

Figure 2:
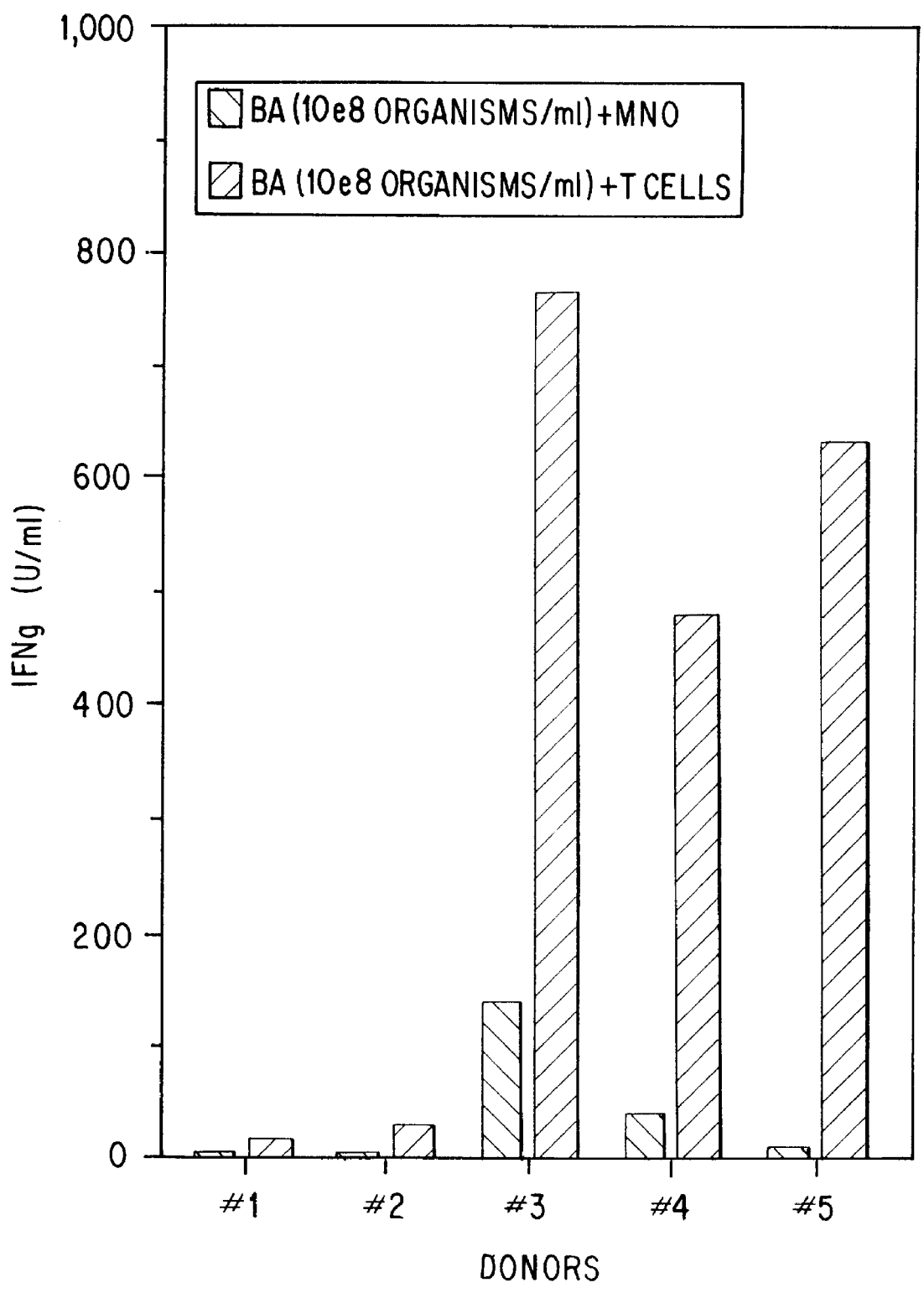
FIG. 2 shows the effect of BA on $IFN_g$ secretion by human peripheral blood T cells, MNC and $E^+$ T cells from five donors were cultured at $10^6$ cells per wall and stimulated with BA ($10^8$ organisms/ml) for five days and the supernatants assayed for $IFN_g$ by ELISA. In the absence of BA (media controls), <0.3 Units of $IFN_g$ was detected in the supernatants from either the MNC or $E^+$ T cell cultures.

In preliminary experiments, the optimal dose for BA was found to be $10^8$ organisms/ml and the peak response was observed between 5–7 days. As can be seen from FIG. 2, in five donors the E+ cells secreted fourfold or more IFNg compared to the MNC. These differences could not be accounted for simply by the T cell enrichment achieved (less than twofold) and were possibly due to removal of a "suppressor cell" by the E-rosetting. The non-rosetting cells, which consisted of 30–40% CD19+ B cells, 40–60% CD14+ monocytes and 15–20% CD3−/CD16+ NK cells, did not secrete more IFNg than the medium control. The reasons for the variations between donors is unknown, but may have been due to the low frequency of BA-responding T cells. In cell titration experiments, cultures containing less than $5 \times 10^5$ cells per well no longer secreted IFNg in response to BA, but still responded to PHA.

The Effect of Macrophage Depletion Upon IFNg Production

To test whether monocytes were acting as suppressors, MNC were passed through a Sephadex G-10 column to deplete monocytes and then cultured with BA. For comparison, undepleted MNC were cultured under identical conditions. The supernatants from both sets of cultures were harvested after five days and assayed for IFNg content. The results are shown below in Table 1. After SEPHADEX G-10 passage, the percentage of monocytes (CD14+) was reduced from 12–18% to <2% (by an average of 88%) and the percent of T cells (CD3+) cells was increased from 40–60% to 70–80% (by an average of 39%). In each of these three experiments the amount of IFNg produced by MNC depleted of monocytes, in response to either concentration of BA, was at least fourfold greater than that of the undepleted MNC. Such large increases in IFNg production suggest that the T cell enrichment was insufficient to account for such enhancement and it was more likely the result of the removal of the suppressive influence of monocytes. When monocytes were added back to T cells the IFNg responses to BA and PHA were decreased.

The inhibitory effects of the monocytes seen in vitro probably reflect the relatively high number of monocytes in MNC preparations. The lymphoid organs in vivo have fewer monocyte/macrophage cells per T cell and they are more differentiated than those in the peripheral blood, so that these cells would be less likely to suppress similar responses in vivo.

TABLE 1

Effect of MO depletion on the ability of T cells to secrete IFNg in response to BA[b]

| Cells | Stimulus | IFNg (U/ml) | | |
|---|---|---|---|---|
| | | Expt. 1 | Expt. 2 | Expt. 3 |
| MNC | Medium | <0.3 | <0.3 | <0.3 |
| | PHA | 124 | 109 | 351 |
| | BA | 228 | 7 | 20 |
| MNC/G10 | Medium | <0.3 | 10 | 43 |
| | PHA | 433 | 826 | 2263 |
| | BA | 959 | 167 | 413 |

[a]Passage of MNCs through Sephadex G-10 (MNC/G10) reduced the mean percentage of monocytes present in three experiments from 18% to 2.2% as determined by flow microfluorimetry. The cells were then cultured at $10^6$ cells per wall for five days with BA and the supernatants assayed for IFNg by ELISA.
[b]BA used at $10^8$ organisms/ml.

IFNg Production by CD4+ and CD8+ T Cells

Figure 3:
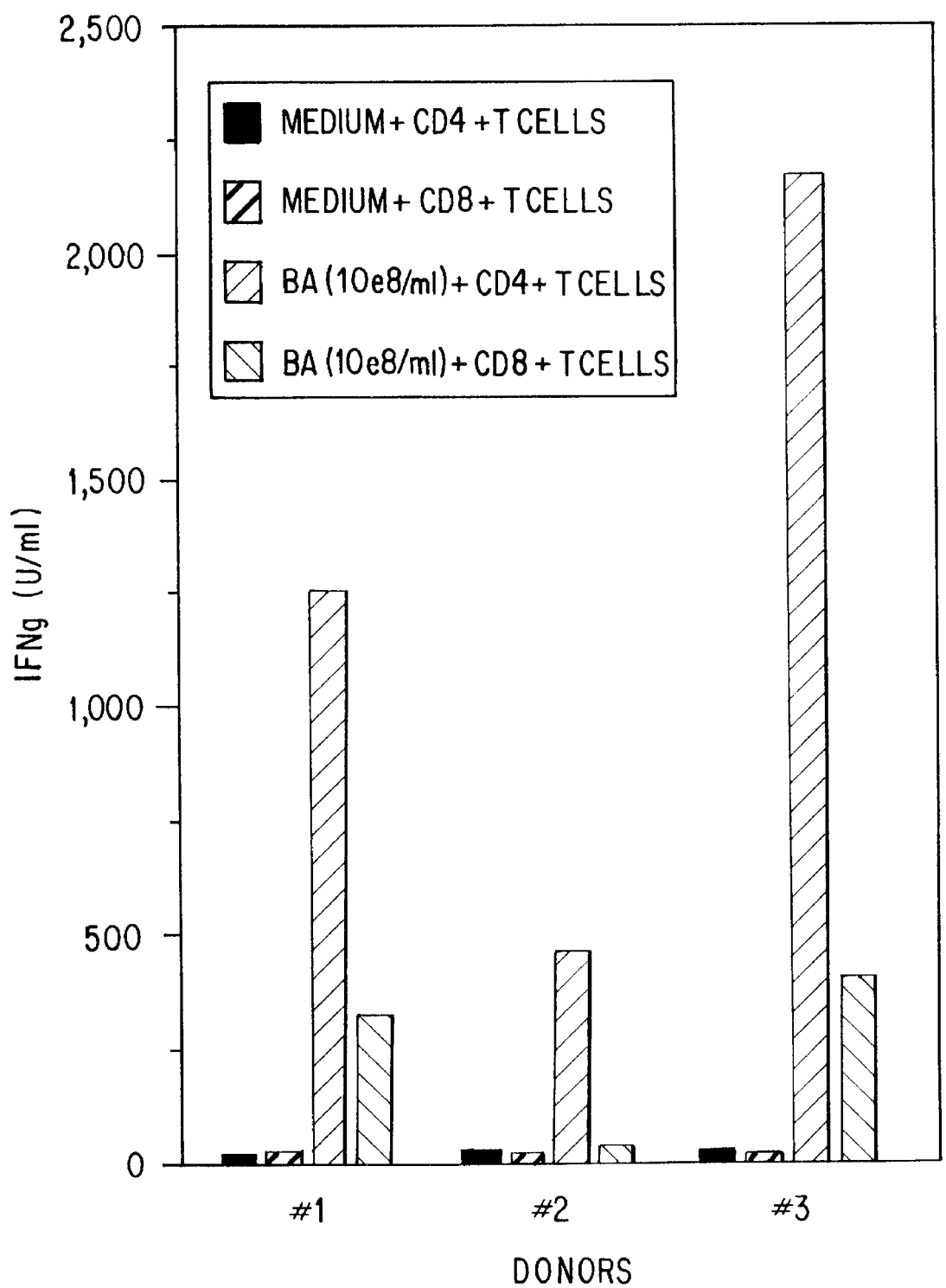
FIG. 3 shows the effect of BA on $IFN_g$ secretion by human peripheral blood CD4+ and CD8+ T cells. $E^+$ T cells from three donors were separated by panning into CD4+ and CD8+ T cells, cultured in the absence or presence of BA ($10^8$ organisms/ml) for five days, and the supernatants assayed for $IFN_g$ by ELISA.
Figure 4:
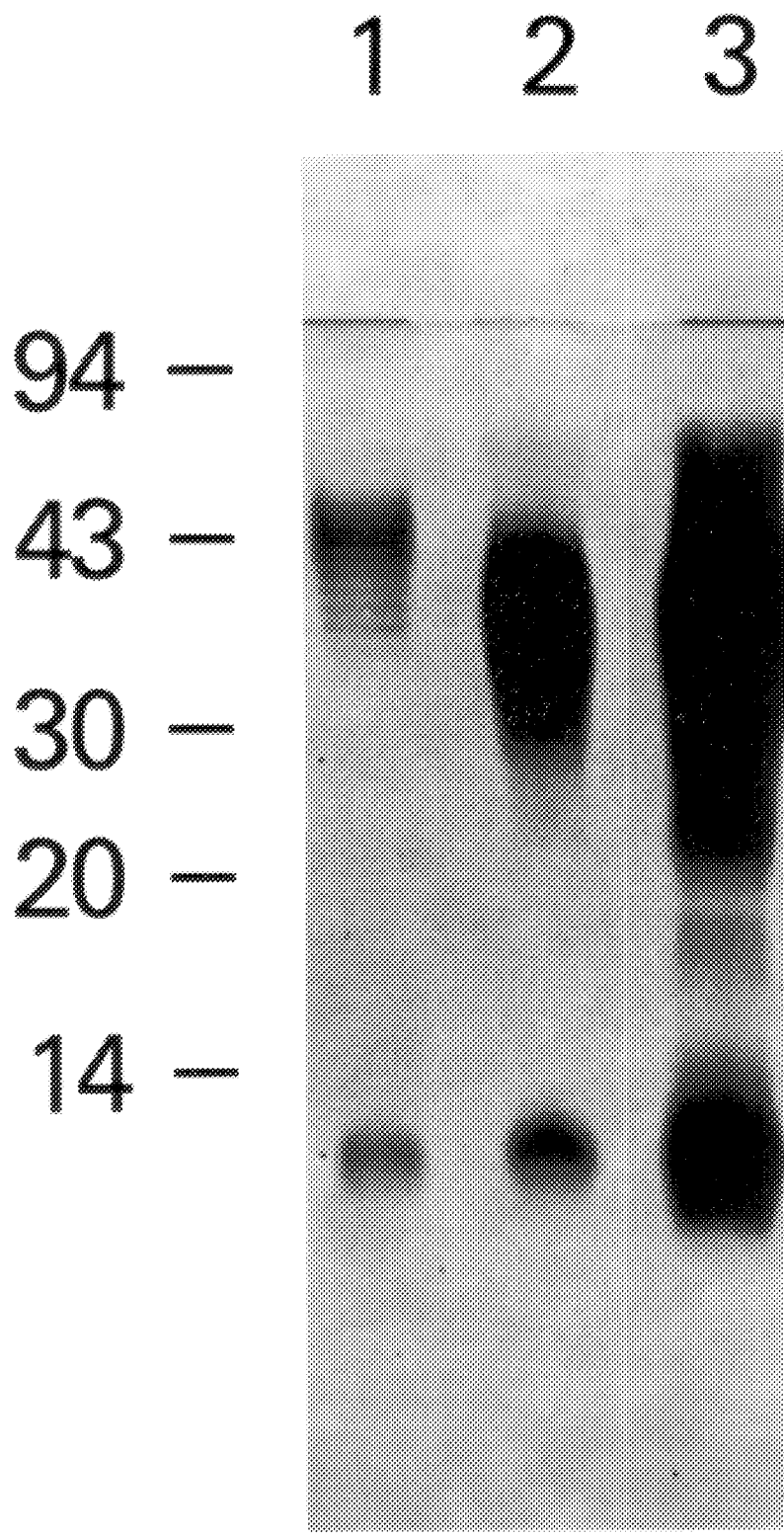
FIG. 4 shows a gel of LPS from *Brucella Abortus*. Lane 1: lipopolysaccharide (LPS) from *Escherichia coli* at 2.5 $\mu$g. Lane 2: LPS-BA at 5. $\mu$g. Lane 3: LPS-BA at 10 $\mu$g.
Figure 5:
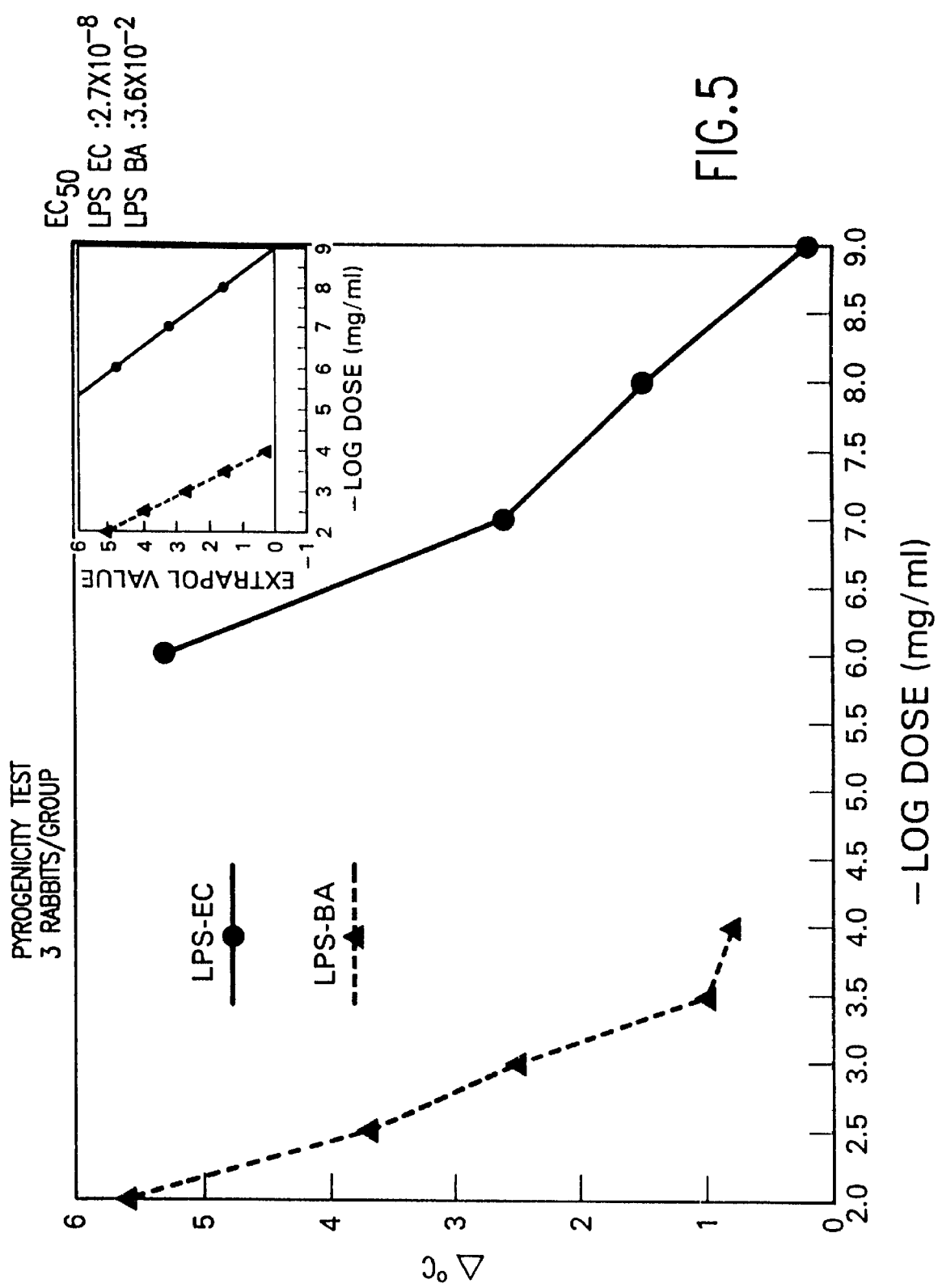
FIG. 5 is a comparison of fever induced in rabbits as a result of I.V. injection of LPS-BA or LPS-EC. Groups of 3 rabbits each were inoculated with increased doses of either LPS. Temperature increases were recorded for 3 hr. The insert shows the regression analysis (r=0.95).

To determine which T cell subpopulation was responding, BA was added to cultures of CD4+ and CD8+ T cells. As depicted in FIG. 3 in three separate experiments, both the CD4+ and CD8+ T cells secreted IFNg following stimulation with BA. In these experiments, CD4+ T cells secreted four to sixfold more IFNg than the CD8+ T cells. The response of the CD8+ cells was not due to contaminating CD4+ T cells since they contained <5% CD4+ T cells. It was possible that some CD4+ T cells bound unlabelled anti-CD4 antibody but failed to adhere to the plate in the panning procedure and were included in the non-adherent CD8+ population. This possibility was excluded by demonstrating that cells treated with anti-CD4 that did not adhere to the plate (coated with goat anti-mouse antibody) did not have increased numbers of cells staining with FITC-labeled goat anti-mouse antibody. Thus, these results show that both CD4+ and CD8+ human T cells are capable of responding to BA and secreting IFNg, although CD4 cells secrete more IFNg.

Effect of Anti-Tac on the Ability of BA-stimulated T Cells to Secrete IFNg

Since TH1 cells have been characterized as secreting both IFNg and IL-2(Street et al., 1990 J. Immunol. 144:1629–1639), and since BA treatment of mice in vivo could expand the number of TH1 cells, it was of interest to determine whether IL-2 was secreted following BA stimulation of human T cells. In addition, it has been shown that IL-2 can induce IFNg secretion from activated T cells (Le et al., 1986 J. Immunol. 136:4525–453), and it was possible that IL-2 was involved in BA-medicated IFNg release. Supernatants of BA-stimulated human T cells did not contain detectable IL-2. This lack of IL-2 detection may have been due to secretion of a relatively small amount of IL-2 that was absorbed by IL-2 receptor bearing T cells. To test this possibility, anti-IL-2 receptor (anti-Tac) was added to BA-stimulated cultures. In the presence of anti-Tac, BA-induced IFNg production was inhibited by 73% or more (Table 2). These data suggest that IL-2 was secreted in response to BA. Furthermore, these results show that IL-2 is required for optimal IFNg secretion by human T cells in response to BA.

TABLE 2

Effect of anti-Tac on the ability of BA-stimulated T cells to secrete IFNg

| Expt. | Added | Anti-Tac[a] | IFNg(U/ml) | % Inhibition |
|---|---|---|---|---|
| 1 | Media | – | 0 | |
| | " | + | 0 | 0 |
| | BA[b] | – | 20 | |
| | " | + | 5 | 75 |
| | PHA[c] | – | 559 | |
| | " | + | 92 | 84 |
| 2 | Media | – | 0 | |
| | " | + | 0 | 0 |
| | BA | – | 96 | |
| | " | + | 8 | 92 |
| | PHA | – | 1054 | |
| | " | + | 92 | 91 |
| 3 | Media | – | 0 | |
| | " | + | 0 | 0 |
| | BA | – | 183 | |
| | " | + | 50 | 73 |
| | PHA | – | 1068 | |
| | " | + | 659 | 38 |

Supernatants were harvested on day 5 and IFNg measured by ELISA.
[a]Anti-Tac was added at the onset of culture at 10 ug/ml.
[b]BA was added at the onset of culture at $10^8$ organisms/ml.
[c]PHA was added at the onset of culture at 10 ug/ml.

Effect of BA on IFNg Secretion by T Cell From HIV-infected Individuals

Since there was evidence from murine studies that BA may be useful as a carrier for HIV-1 antigens (Golding et al., 1991 Aids and Human Retroviruses 7: 471–482) and because the IgG isotypes obtained was shown to be influenced by IFNg, it was important to determine whether BA would evoke IFNg secretion by T cells from HIV-infected persons. Table 3 shows that BA could induce IFNg secretion from eight of nine HIV-infected asymptomatic persons, including two individuals with low CD4+ T cell numbers (#5 and #8). In contrast, BA did not evoke IFNg secretion in four HIV-infected symptomatic persons (Table 4). However, in the presence of IL-2, BA was able to elicit IFNg secretion from T cells of these individuals. This response was apparent even though these individuals had reduced CD4/CD8 ratios, symptoms of HIV-1 infection, and two of them lacked in vitro responses to influenza virus. These results indicate that BA is capable of stimulating T cells from HIV-infected persons to release IFNg; however, in symptomatic individuals, an additional signal, provided by IL-2, is required.

TABLE 3

Effect of Brucella abortus on IFNg production by T cells[a] from HIV-1 infected[b] asymptomatic individuals

| | IFNg (U/ml) | | | | | | | | |
|---|---|---|---|---|---|---|---|---|---|
| | #1 | #2 | #3 | #4 | #5 | #6 | #7 | #8 | #9 |
| Medium | <0.3 | <0.3 | 11 | 26 | <1 | 54 | 34 | 60 | 40 |
| BA ($10^a$ organisms/ml) | 30 | 62 | 7 | 81 | 19 | 232 | 62 | 320 | 205 |
| PHA (10 ug/ml) | 224 | 216 | 224 | 154 | 330 | 130 | 250 | 520 | 480 |
| | CD4+ cell numbers | | | | | | | | |
| CD4[c] | 787 | 1003 | 1008 | ND[d] | 230 | ND | ND | 300 | 765 |

[a]Cells were obtained from peripheral blood and subjected to Ficoll-Hypaque separation. The MNC were E-rosetted to obtain T cells which were cultured at $10^6$ cells per well for 7 days.
[b]HIV-1 infection was determined by ELISA and confirmed by immunoblot.
[c]The number of CD4+ T cells per $mm^3$ of whole blood.
[d]ND = Not determined.

TABLE 4

Effect of BA and IL-2 stimulation of T cells from symptomatic HIV-infected individuals

|  | #10 | #11 | #12 | #13 |
|---|---|---|---|---|
| IFNg (U/ml) | | | | |
| Medium | <0.3 | <0.3 | <0.3 | <0.3 |
| PHA[a] | 32 | 16 | 176 | 400 |
| BA[b] | <0.3 | <0.3 | 1 | <0.3 |
| IL-2[c] | <0.3 | <0.3 | 7 | <0.3 |
| BA + IL-2 | 15 | 11 | 56 | 160 |
| Clinical/immunological parameters | | | | |
| CD4/CD8 | 0.6 | 0.34 | 0.67 | 0.75 |
| Flu[d] | + | + | − | − |
| WR[e] | 2 | 3 | 2 | 3 |

[a]PHA at 10 ug/ml.
[b]BA at 108 organisms/ml.
[c]IL-2 at 20 U/ml.
[d]Flu indicates the IL-2 response to influenza antigen (+ represents a threefold or greater response than the medium control)
[e]Walter Reed classification.

Extraction of Brucella abortus LPS

Crude LPS from live cells of *B. abortus* strain 1119 was obtained from the Department of Agriculture, Ames, Iowa and extracted by the n-butanol-water procedure as described by Morrison and Leive (Morrison and Leive, 1978 J. Biol. Chem. 250:2911–2919) and recently modified by Phillips using Proteinase K to reduce the protein content (Phillips et al., 1989 Amer. J. Vet. Res. 50:311–317). This butanol-water partition procedure is considered a mild extraction in which the cells are not being disrupted.

Briefly, 50 grams of live cells were centrifuged in 400 ml of water saturated n-butanol (99%) at 4° C. The water phase was extracted, centrifuged to removed insoluble material and pooled. To precipitate LPS, 4 vol. of methanol were added. This precipitate was dissolved in 0.1M Tris (pH 8) containing 2% SDS and 2% mercaptoethanol, heated 5 min at 100° C. and 90 min at 60° C. After overnight treatment with proteinase K, the material was washed twice with cold methanol, dissolved in water and ultracentrifuged at 150, 000g for 8 hours. The pellet was redissolved in water and freeze-dried.

Lipopolysaccharide from *Escherichia coli* strain 235 was purchase from List Biological Laboratories (Campbell, Calif.)

LPS-BA Chemical Analysis

Protein content of the LPS thus obtained was estimated by the method of Lowry et al. (Lowry et al., 1951 J. Biol. Chem. 193:265–275) using bovine serum albumin as a standard. Ketodeoxy-octonate (KDO) content was determined by the methods described by Osborne (Osborn et al., 1972 J. Biol. Chem 247:3962–3972; Osborne M. J., 1963 Proc. Natl. Acad. Sci. 50:499–506) using KDO (Sigma) standard for determination of KDO. Nucleic acid was estimated by absorption at 259 nm. SDS-PAGE electrophoresis was also performed on Novex pre-cast gels 16%, 1.5 mm using also Novex buffer (Novex, Encinitas, Calif.) and run according to Laemmli specifications (Laemmli U. K., 1970 Nature. 227:680–685). Lanes were loaded with 10 $\mu$g of the preparation. Gels were stained with either Coomassie blue or with a modified silver stain (Tsai et al., 1982 Anal. Biochem. 19:115–119).

Limulus Amebocyte Lysate Test

This test was performed by the Division of Quality Control at the FDA following the U.S. Pharmacopeia (USP) "Bacterial Endotoxin Test" and the U.S. FDA Guideline for LAL testing (Guideline on validation of the limulus amebocyte lysate test as an end product. Endotoxin test for human and animal parental drugs, biological products and medical devices. U.S. Department of Health and Human Services, F.D.A., December 1987), that provide standard methods for validating this assay. The basis of this assay is the gelation produced by LAL in the presence of endotoxin. This procedure is time and endotoxin concentration dependent.

Control Standard Endotoxin derived from *E. coli* are serially diluted to 1 EU/ml. Reconstituted LAL (0.1 ml) is added to each tube assayed in duplicates starting with the negative control and ending with the highest endotoxin concentration. Tubes are incubated at 37° C. for 60 minutes. A positive test is defined as the formation of a firm gel capable of maintaining its integrity when the test tube is inverted 180°. A negative test is defined by the absence of gel or by the formation of a viscous mass which does not hold together when the tube is inverted.

LPS contained less than 1% of protein by weight and the nucleic acid contamination was <1% at 260 nm. The LAL test showed $6\times10^6$ E.U./ml. KDO, which is a unique component of bacterial LPS, was found to be 1% by weight.

SDS-PAGE Electrophoresis

In the presence of SDS (FIG. 4), the high molecular weight aggregates of LPS dissociate into monomers complexed with SDS due to hydrophobic binding of SDS to the lipid A of LPS (Morrison et al., 1990 J. of Inf. Diseases. 162:1063–1068). The negatively charged LPS-SDS complex migrates in the polyacrylamide gel towards the anode. LPS-BA O-chain is composed of a single unique glycose repeating unit. The A antigen is a linear unbranched homopolymer of 1,2-linked 4,6 D-mannosapyranosyl units terminated at its reducing end by a minor core oligosaccharide component (Caroff et al., 1984 Infect. Immun. 46:384–388).

SDS-PAGE performed on 16% pre-cast gels and stained with silver stained, correlates with the chemical composition described above: the profile consisted of a fast migrating band of low-$M_r$ that represent the lipid A-core oligosaccharide portion. The slow migrating components appeared as a smear and indicate the presence of the O-side chain composed of increasing numbers of a single repeating unit. Two thick bands were seen at 25,000$M_r$. These probably represent the covalently bound protein described by Perera et al. (Nawroth et al., 1984 FEMS Microbiol. Lett. 21: 263–266). This pattern correlates with the one previously described (Phillips et al., 1989 Amer. J. Vet. Res. 50:311–317).

Rabbit Pyrogen Test

This procedure was performed as previously described (Code of Federal Regulation, 1989, Chapter 1, 610–613) on ten groups of rabbits, each group consisting of 3 rabbits. Briefly, 2.5 to 3 kilogram rabbits were injected with either LPS-BA or LPS-EC at concentrations of 100, 10, 1, 0.1, 0.01 $\mu$g/ml in 3 ml/kg of body weight.

After 30 minutes each group was inoculated with an ear vein I.V. The groups were then observed for changes in their body temperature every hour for three hours (FIG. 5). The temperature determined as base line was recorded at time 0. The test suggests presence of pyrogen if one of the three rabbits has an increase in body temperature higher than 0.6° C. or if the sum of the three individual rabbits' maximum temperature rise exceeds 1.4° C. The $EC_{50}$ for LPS-EC, obtained from the regression analysis (r=0.97) was $2.7\times10^{-7}$ and for the $EC_{50}$ for LPS-BA was $3.6 \times 10^{-3}$. This suggests that LPS-BA is approximately 10,000 fold less pyrogenic than LPS-EC and less likely to induce endotoxic shock.

Mice Lethality

To determine differences in lethality, groups of ten C3H/HeN male mice were injected intraperitoneally and simultaneously with 18 mg of D-galactosamine (Sigma) per mouse and increasing doses of LPS from either Brucella abortus or E. coli (Freudenberg M. A. and C. Galanos, 1988 Infec. Immun. 56:1352–1357; Lehmann et al., 1987 J. Exp. Med. 166:657–663; Galanos et al., 1979 Proc. Natl. Acad. Sci. 76:5939–5943) in 0.2 ml of PBS. Following the injection mice were observed for 72 hr.

Mice injected with D-galactosamine and increasing doses of LPS were observed for a period of 3 days (FIG. 6). In the group inoculated with LPS-EC the lowest dose that induced endotoxic shock was 0.1 μg/mouse (20% dead) (FIG. 6). The lowest dose that killed 100% of the mice for LPS-EC was 3 μg/mouse. The LD50 for LPS-EC was determined to be 336.4 ng per mouse, whereas the LD50 for LPS-BA was 90,064 ng per mouse. Therefore, LPS-EC was 267.7 times more potent than LPS-BA in causing lethality in mice.

IL-1β and TNF-α Assays

To determine their effect on IL-1β secretion by human cells, LPS-BA and LPS-EC were added to MNC and tested for IL-1β production. Human peripheral blood monocytes were prepared at the NIH Clinical Center (Bethesda, Md.) by countercurrent centrifugal elutriation using techniques which are designed to yield large numbers of purified monocytes suitable for clinical use, as described (Abrahamsen et al., 1989 J. Clin. Aphar. 51:891–895).

Briefly, peripheral blood mononuclear cells from leukapheresis were isolated by using an automated Ficoll-Hypaque density gradient centrifugation. Elutriation was performed in a model J-6M centrifuge (Beckman Instruments, Palo Alto, Calif.) equipped with a JE-5.0 rotor operating at 1440×g. Monocytes were collected in Hanks' Balanced Salt Solution (HBSS) without $Ca^{2+}$ and $Mg^{2+}$ at a flow rate of 160 ml/minute. Monocytes obtained by this method were greater than 90% pure as assessed by histochemical staining. Contaminating cells consisted mainly of lymphocytes and some (<2%) granulocytes.

MNC were plated at $4 \times 10^5$/per well in Iscove's medium supplemented with 5% human AB serum, 0.1% HSA or medium alone were incubated in 96 well Costar plates with LPS-BA and LPS-EC for 18 hours. Total IL-1β (extracellular and cell-associated) and TNF-α was measured by ELISA (Cistron Biotechnology, Pine Brook, N.J.).

Supernatants of stimulated monocytes were added to 96-well microtiter plates coated with monoclonal antibody specific for IL-1β or TNF-α and incubated for 2 hours at 37° C. in 5% $CO_2$ after which the wells were washed three times with wash buffer. Polyclonal rabbit anti-IL-1β was then added. The antibody binds to the solid phase if IL-1β was then added. The antibody binds to the solid phase if IL-1β or TNF-α is present. After a second incubation and washing step, goat anti-rabbit IgG conjugated to horseradish peroxidase is added. In the last step, the enzyme substrate is added to the walls.

If the bound conjugate is present, the substrate will be oxidized and color development is proportional to the amount of bound conjugate and therefore, to the amount of IL-1β or TNF-α present in the sample. The amount of monokine present in each sample is determined by interpolation from a standard curve using known amounts of IL-1β of TNF-α. Plates were read in a Vmax™ Kinetic Microplate Reader (Molecular Devices Corporation, Palo Alto, Calif.) at 405 nm.

The limit of sensitivity of these assays was determined by Cistron to be 20 pg/ml. IL-1β maximum production was achieved with LPS-EC at concentrations of 1 ug/ml producing 13,652 pg/ml of this monokine. In contrast, the maximum concentration of IL-1β reached in response to LPS-BA wa 7,144 μg/ml (FIG. 7a) using a dose of 100 μg/ml.

Figure 7:
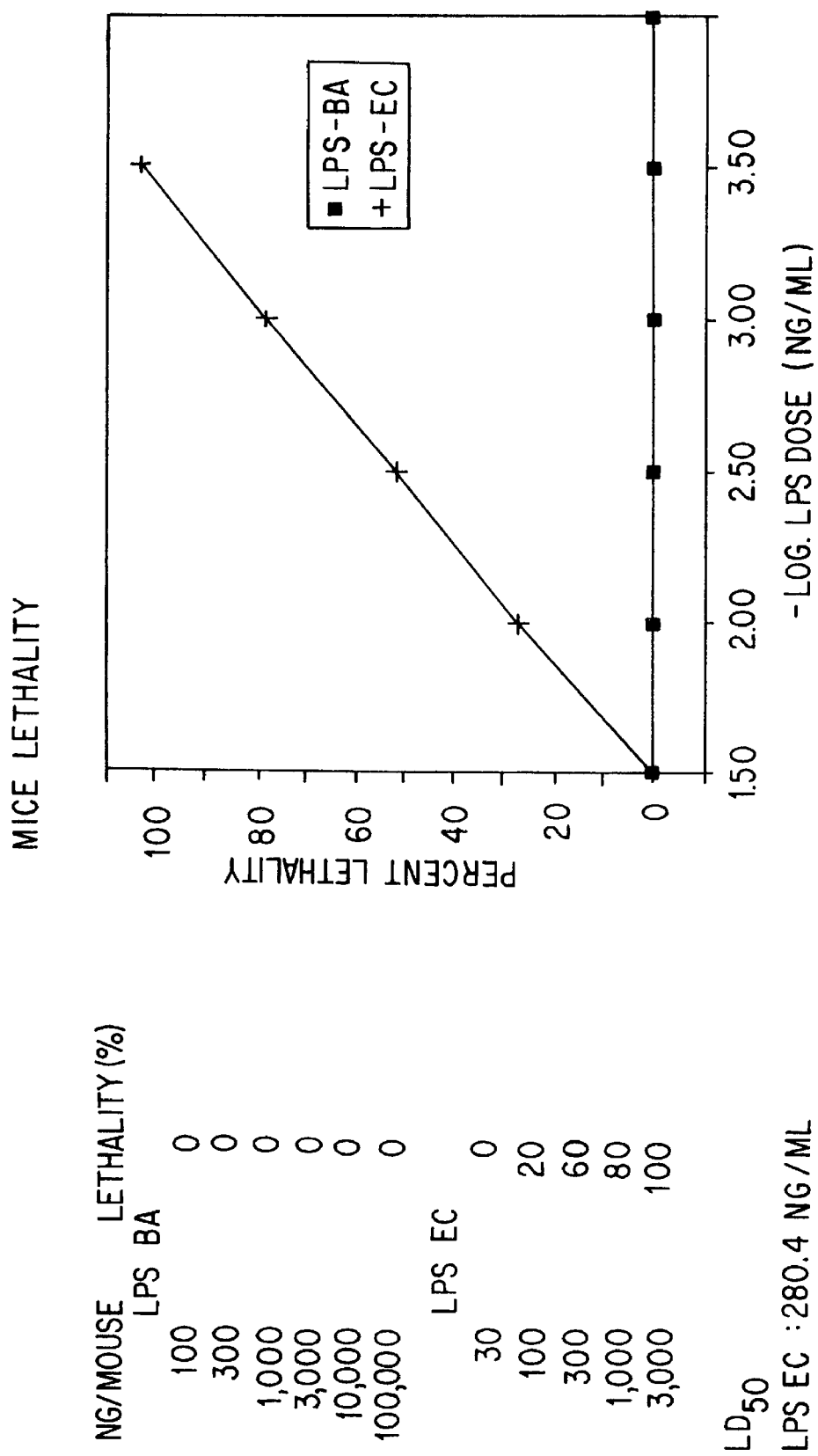
FIG. 7 is a comparison of effect of LPS-BA and LPS-EC on mouse lethality. Groups of 5 mice were injected with increasing doses of either LPS simultaneously with D-galactosamine and observed for 3 days (r=0.98).

The dose response of LPS-BA and LPS-EC were compared by regression analysis in terms of IL-1β production. The results are expressed as a percentage of the maximal response (FIG. 7a). The dose of LPS-EC that induced 50% of the response ($EC_{50}$) was 0.007 μg/ml whereas the $EC_{50}$ for LPS-BA was 10 μg/ml. These results demonstrated that LPS-EC is at least 1400-fold more potent than LPS-BA in inducing IL-1β production in human monocytes.

The response to LPS-EC and LPS-BA in terms of TNF-α release was also compared by regression analysis (FIG. 7b). The results are expressed as a percentage of the maximal response. The $EC_{50}$ for LPS-EC was 0.0023 μg/ml whereas the $EC_{50}$ for LPS-BA was 1 μg/ml. Based on these results LPS-EC was shown to be 400-fold more potent than LPS-BA in inducing TNF-α secretion. These results suggest that LPS-BA is less likely than LPS-EC to induce endotoxic shock because it is less potent in stimulating release of IL-1β and TNF-α from human monocytes.

LPS-BA as Carrier for TNP

Trinitrophenol (TNP) was conjugated to LPS by adding trinitrobenzene sulphonic acid (TNBS) to LPS in a ratio of 2:1 by weight for 10 min at 25° C. The material was the passed through a SEPHACRYL 20 column to separate the TNBS from the TNP-LPS.

TNP-LPS form B. abortus, TNP-LPS (BA), and TNP-LPS form E. coli was injected three times into BALB/c mice at 2 week intervals. Five days after the third immunization mice were bled and their sera tested for anti-TNP antibodies by ELISA.

As seen in Table 5, LPS from BA functions as an immunological carrier for haptens such as TNP. Further, when used as a carrier LPS-BA was shown to be almost (2.6 fold less) as potent as LPS-EC. This is in marked contrast to the results of toxicity assays (see above), in which LPS-EC was 268 to 10,000 fold more potent, depending on which assay was employed.

TABLE 5

Comparison of LPS-BA and LPS-EC as carriers for TNP in IgG anti-TNP responses.

| Dose (μg/ml) | IgG Titer | |
|---|---|---|
| | TNP-LPS (BA) | TNP-LPS (EC) |
| 0 | 200 | 200 |
| 6.25 | 400 | 6,400 |
| 12.5 | 3,200 | 800 |
| 25 | 12,800 | 25,600 |
| 50 | 25,600 | 102,400 |
| 100 | 51,200 | 409,600 |

Human T cells were stimulated with B. abortus, LPS from B. abortus and LPS from E. coli. All three of these stimuli elicited interferon-gamma release, especially in the presence of IL2 (see FIG. 8). This may be important, because IFNg has many actions on immune system cells including increased differentiation of human antibody producing cells.

All publications mentioned hereinabove are hereby incorporated by reference.

the foregoing invention has been described in detail for purposes of clarity and understanding. However, it will be appreciated that those skilled in the art, upon consideration of this disclosure, may make modifications and improvements without departing from the true scope of this invention.

What is claimed is:

1. A conjugate molecule comprising a carrier molecule of purified lipopolysaccharide (LPS) from *Brucella abortus,* covalently coupled to an antigenic component of an infectious organism, a tumor antigen or a biological effector molecule.

2. The conjugate according to claim 1 wherein said carrier is purified at least 95%.

3. The conjugate according to claim 2 wherein said carrier is purified at least 98%.

4. The conjugate according to claim 1 wherein said carrier and said component are coupled via heteroligation using thio-ester linkages.

* * * * *